US 6,676,613 B2

(12) United States Patent
Cantrell et al.

(10) Patent No.: US 6,676,613 B2
(45) Date of Patent: Jan. 13, 2004

(54) CHEST MOUNTED CARDIO PULMONARY RESUSCITATION DEVICE AND SYSTEM

(76) Inventors: Elroy T. Cantrell, 33 Lakeview Manor, Huntsville, TX (US) 77340; Jon Spijkerman, 1014 Briarcliff Dr., Arlington, TX (US) 76012

( * ) Notice: Subject to any disclaimer, the term of this patent is extended or adjusted under 35 U.S.C. 154(b) by 145 days.

(21) Appl. No.: 09/788,813

(22) Filed: Feb. 20, 2001

(65) Prior Publication Data

US 2001/0011159 A1 Aug. 2, 2001

Related U.S. Application Data

(62) Division of application No. 09/173,622, filed on Oct. 16, 1998, now Pat. No. 6,174,295.
(60) Provisional application No. 60/062,299, filed on Oct. 17, 1997.

(51) Int. Cl.⁷ ............................................. A61H 31/00
(52) U.S. Cl. ............................................ 601/41; 601/44
(58) Field of Search .............................. 601/41–44, 134, 601/135, 107, 108; D24/167; 128/204.21

(56) References Cited

U.S. PATENT DOCUMENTS

| 443,204 A | 12/1890 | Davis |
|---|---|---|
| 2,484,306 A | 10/1949 | McClain et al. |
| 3,307,541 A | 3/1967 | Hewson |
| 3,489,140 A | 1/1970 | Mullikin |
| 3,552,390 A | 1/1971 | Muller |
| 4,297,999 A | 11/1981 | Kitrell |
| 4,397,306 A | 8/1983 | Weisfeldt et al. |
| 4,424,806 A | 1/1984 | Newman et al. |
| 4,702,231 A | 10/1987 | Arpin |
| 4,770,164 A | 9/1988 | Lach et al. |
| 4,809,683 A | 3/1989 | Hanson |
| 4,915,095 A | 4/1990 | Chun |
| 5,295,481 A | 3/1994 | Geeham |
| 5,327,887 A | 7/1994 | Nowakowski |
| 5,399,148 A | 3/1995 | Waide et al. |
| 5,454,779 A | 10/1995 | Lurie et al. |
| 5,487,722 A | 1/1996 | Weaver, II et al. |

(List continued on next page.)

FOREIGN PATENT DOCUMENTS

SU             321253       * 11/1971   .................. 601/41

OTHER PUBLICATIONS

Todd J. Cohen, M.D. et al., "Active Compression–Decompression, A New Method of Cardiopulmonary Resuscitation," JAMA, Jun. 3, 1992, p. 2916, vol. 267, No. 21.

(List continued on next page.)

Primary Examiner—Danton D. DeMille
(74) Attorney, Agent, or Firm—Vinson & Elkins L.L.P.

(57) ABSTRACT

The Chest-positioner/pad Cardio Pulmonary Resuscitation System (CCPRS) provides improved resuscitation during one-person or two-person CPR. The simple, compact, portable and cost-effective system provides for manual, mechanical or electrical driven external chest compressions via a socket connection to a chest-positioner/pad unit. The chest-positioner/pad unit provides greater control of compression positioning providing adequate and reproducible chest compressions while preventing rib fractures and damage to vital internal organs. A module gives providers feedback to enable a provider to apply an appropriate compressive force in an appropriate direction, recurringly under emergency conditions. The present invention also provides improved blood circulation, oxygenation and gas exchange by expanding the chest past its normal relaxation point during diastole. Providers are able to administer adequate CPR for longer periods of time with reduced or minimal effort while improving survivability of cardiac arrest victims.

11 Claims, 15 Drawing Sheets

U.S. PATENT DOCUMENTS

| | | | |
|---|---|---|---|
| 5,496,257 A | | 3/1996 | Kelly |
| 5,589,639 A | | 12/1996 | D'Antonio et al. |
| 5,634,886 A | | 6/1997 | Bennett |
| 5,645,522 A | | 7/1997 | Lurie et al. |
| 5,738,637 A | | 4/1998 | Kelly et al. |
| 5,820,572 A | * | 10/1998 | Palmer |
| 6,125,299 A | | 9/2000 | Groenke et al. ............. 607/6 |

OTHER PUBLICATIONS

Todd J. Cohen, M.D. et al., "A Comparison of Active Compression–Decompression Cardiopulmonary . . . ", N. Engl. J Med, Dec. 23, 1993, pp. 1918–1921, vol. 329.

Karl H. Lindner, M.D. et al., "Effects of Active Compression–Decompression Resuscitation on Myocardial . . . " Circulation, 1993, vol. 88, pp. 1254–1263.

J.M. Christenson, M.D. et al., "Abdominal Compressions During CPR: Hemodynamic Effects of Altering Timing . . . " The Journal of Emergency Medicine, 1992, vol. 10, pp 257–266.

Lars Wik, "Effects of various degrees of compression and active decompression on haemodynamics, end–. . . " Elsevier Science Ireland Ltd., 1996.

* cited by examiner

CHEST MOUNTED CARDIO PULMONARY RESUSCITATION DEVICE AND SYSTEM

This application claims the benefit of and is a divisional of prior U.S. application Ser. No. 09/173,622 filed Oct. 16, 1998 now U.S. Pat. No. 6,174,295 which is based in part on U.S. Provisional Application No. 60/062,299 filed Oct. 17, 1997.

The heart and lungs work together to circulate oxygenated blood. However, the heart may stop due to heart attack, drowning, suffocation and electric shock. Consequently, oxygenated blood may not flow to vital organs, particularly the brain. Brain cells begin to suffer and die within six minutes after the heart stops circulating blood. In the event of heart pumping failure, Cardio Pulmonary Resuscitation (CPR) is often administered to temporarily sustain blood circulation to the brain and other organs during efforts to re-start the heart pumping. This effort is directed toward reducing hypoxic damage to the victim.

Generally, CPR is administered by a series of chest compressions to simulate systole and relaxations to simulate diastole, thereby providing artificial circulatory support. Ventilation of the lungs is usually provided by mouth-to-mouth breathing or by means of an externally activated ventilator. Successful resuscitation is determined primarily by three factors: 1. the time delay in starting treatment, 2. the effectiveness of a provider's technique, and 3. prior or inherent damage to the heart and vital organs. Considering these factors, the present techniques of resuscitation have shortcomings.

Manual CPR as taught in training courses worldwide can be easily started without delay in most cases. When properly administered, basic CPR can provide some limited circulatory support. Unfortunately, there is considerable variability in provider skill, endurance and strength. Furthermore, a person who does not perform CPR very often may not maintain those skills. Even in trained persons there is considerable variation in application of force, timing, and dwell time of the duty cycle. The American Heart Association recommends a 50% dwell time in compression. The position of the hands on the victim's chest may vary or shift during CPR, thereby risking damage to ribs or internal organs and lessening the effectiveness of CPR. With prolonged CPR, provider fatigue may limit effectiveness and indeed, is an indication to terminate rescue efforts.

Various mechanical, electrical, pneumatic, and hydraulic devices have been devised to address these problems and to improve resuscitation efforts. Devices have included chest squeezers, chest thumpers, and sternal depressors in various configurations. Some systems include means for ventilatory support, abdominal counter-pulsation or binding, defibrillation, chest decompression, and electrical monitoring of cardiac electrical activity. A timer device has also been developed which can monitor manually applied CPR forces.

None of the devices reported to date has the capacity to provide all the beneficial functions of CPR; including adequate compressions/decompressions, ventilation, abdominal support, and data logging in a configuration which is compact, portable, mobile, simple, and cost-effective. None of these devices can effectively provide circulatory support in a variety of adverse conditions such as moving ambulances, flying airliners, sports arenas, remote or irregular terrain or woodlands, victims trapped in limited space, or victims in a soft bed.

SUMMARY

The chest-positioner/pad cardio pulmonary resuscitation system (CCPRS) provides improved resuscitation during one-person or two-person CPR. The simple, compact, portable and cost-effective system provides for manual, mechanical or electrical driven external chest compressions via a socket connection to a chest-positioner/pad unit. The chest-positioner/pad unit provides greater control of compression positioning providing adequate and reproducible chest compressions while preventing rib fractures and damage to vial internal organs. The present invention also provides improved blood circulation, oxygenation and gas exchange by expanding the chest past its normal relaxation point during diastole. Providers are able to administer adequate CPR for longer periods of time with reduced or minimal effort while improving survivability of cardiac arrest victims.

Certain embodiments of this invention are not limited to any particular individual features disclosed, but include combinations of features distinguished from the prior art in their structures and functions. Features of the invention have been broadly described so that the detailed descriptions that follow may be better understood, and in order that the contributions of this invention to the arts may be better appreciated. There are, of course, additional aspects of the invention described below. These may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes, addresses and meets the previously-mentioned preferences or objectives in its various possible embodiments and equivalents thereof. To one of skill in this art who has the benefit of this invention's realizations, teachings, disclosures, and suggestions, other purposes and advantages will be appreciated from the following description and the accompanying drawings. The detail in the description is not intended to thwart this patent's object to claim this invention no matter how others may later disguise it by variations in form or additions of further improvements. These descriptions illustrate certain preferred embodiments and are not to be used to improperly limit the scope of the invention which may have other equally effective or legally equivalent embodiments.

DETAILED DESCRIPTION

Figure 1:
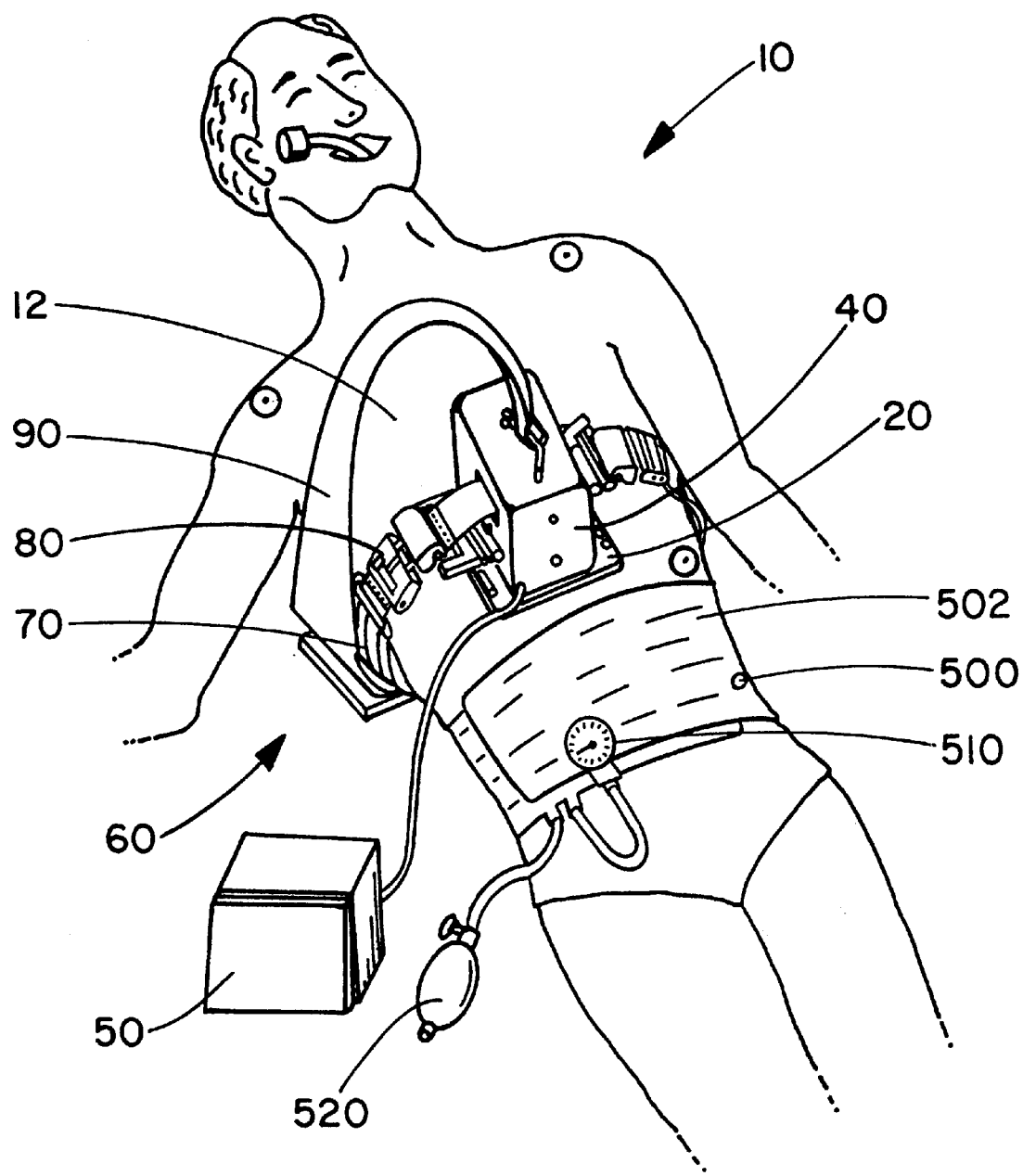
FIG. 1 is a view of a Chest-positioner/pad CPR System (CCPRS) attached to a victim, showing also an endotracheal tube in place for ventilation support, and an adjustable abdominal binding strap.
Figure 2:
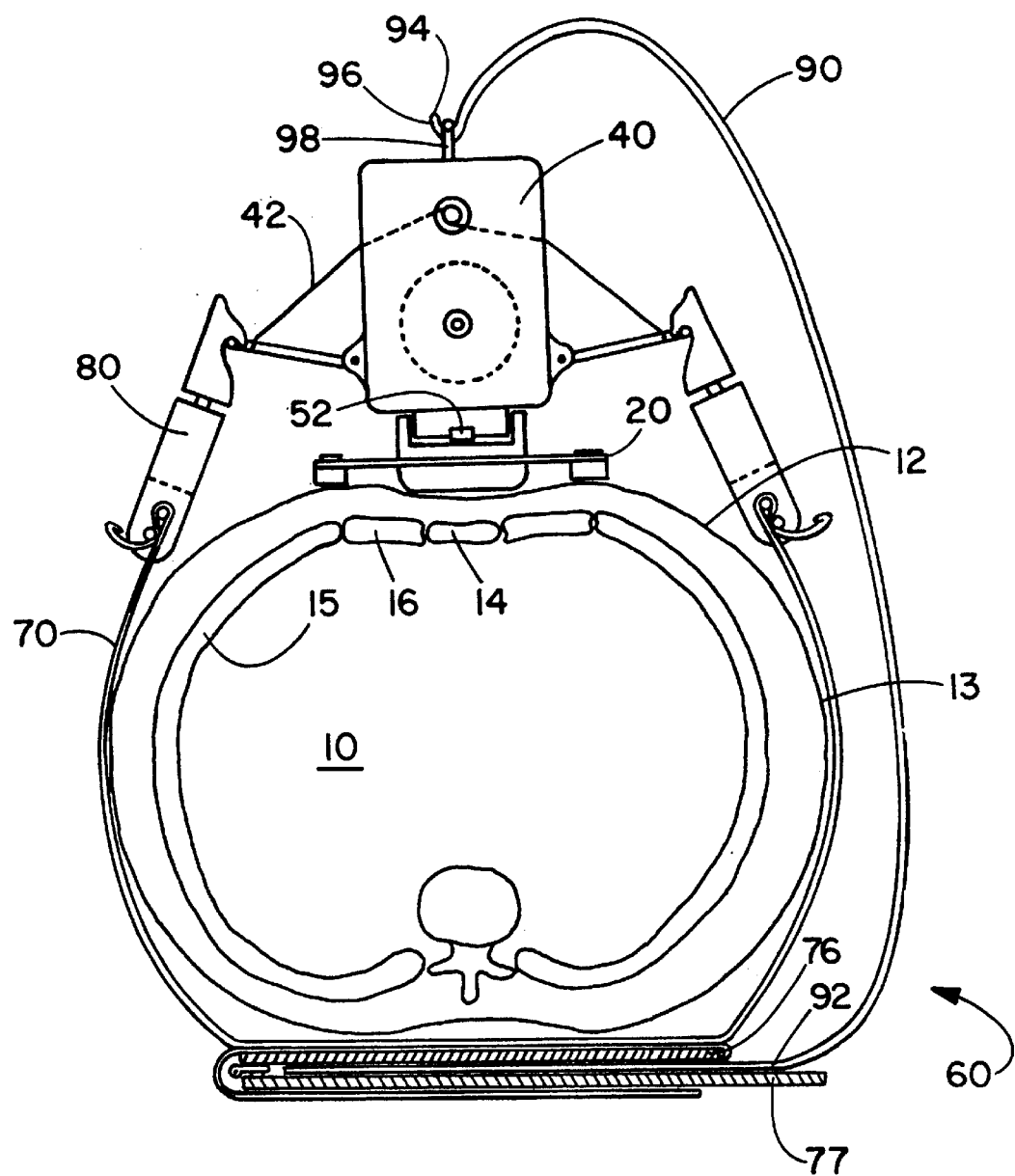
FIG. 2 is a front view of an electrical CCPRS driven by a strap winding shaft, secured to a victim's chest.

Referring to FIGS. 1 and 2, the present invention is for use with a victim 10 in need of CPR and generally comprises a chest-positioner/pad 20 (referred to below as chest-positioner/pad unit 20), compression device 40, control system 50, an assembly 60 for securing the compression device 40 to victim 10, dorsal strap 70, connector 80 and recoil spring 90 for exerting an upward recoil force to lift the compression device 40 and victim's anterior chest wall 12. A pressure sensor 52 is located in the base of the compression device 40.

Figure 3:
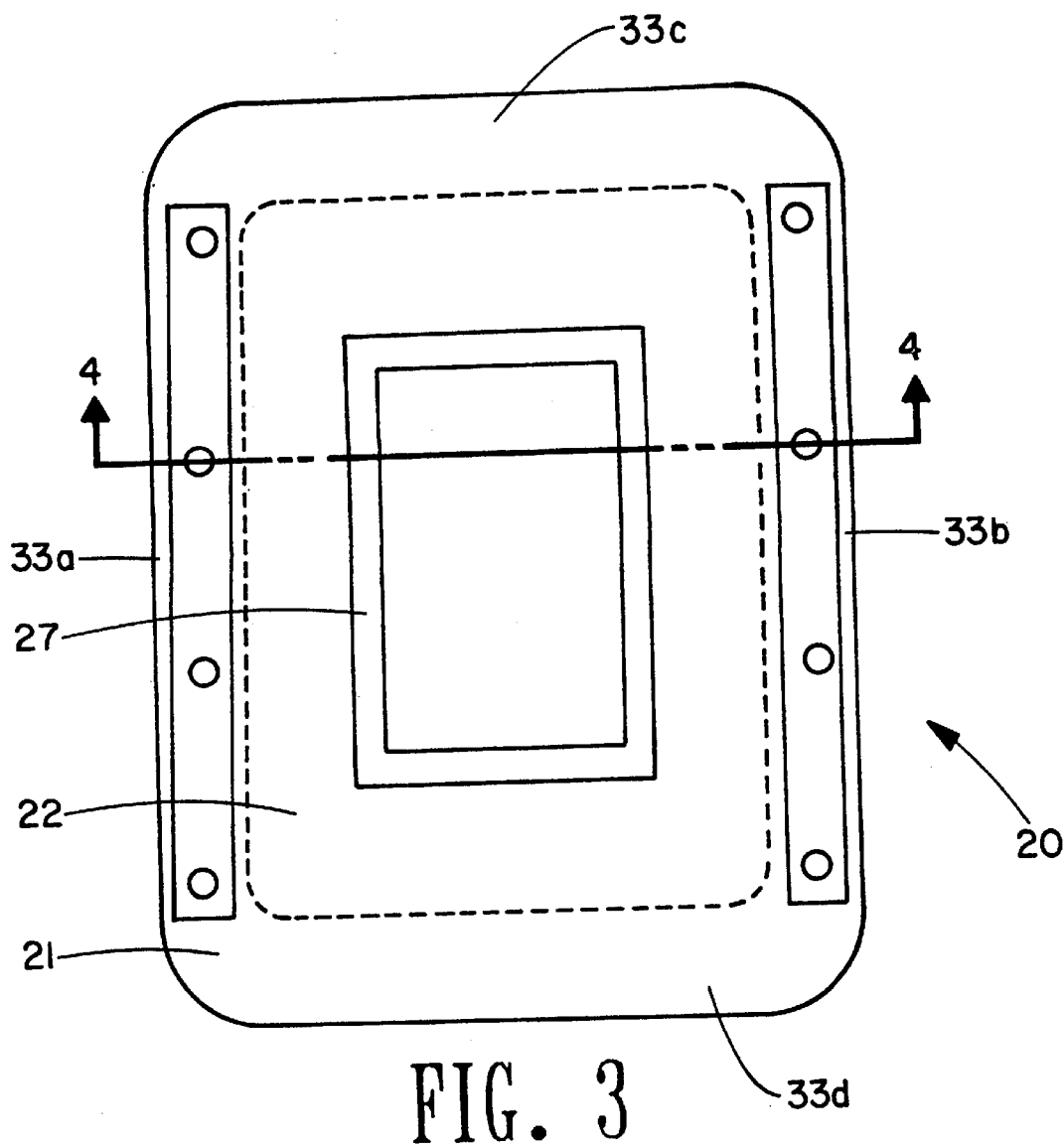
FIG. 3 is a top view of the "chest-positioner/pad" chest positioner/pad.
Figure 4:
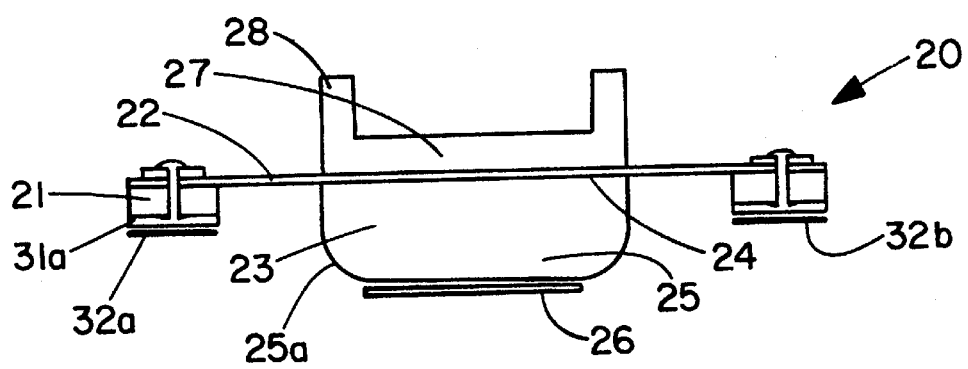
FIG. 4 is a cross-sectional view of the chest-positioner/pad chest positioner/pad taken along line 4—4 of FIG. 3.

Referring to FIGS. 3 and 4, chest-positioner/pad unit 20 generally comprises a rim 21, elastic sheet 22, sternal pad 23, and socket 27. The primary functions of the chest-positioner/pad unit 20 are: (1) to protect the thorax 13 including the ribs 15, costal cartilages 16, sternum 14, and internal organs (not shown), and (2) to provide a stable platform for the compression device 40. Other designs for a chest-positioner/pad unit which achieve these same functional features may be incorporated into the invention.

The rim 21 is shaped like a rectangular ring. The outer boundary of the rim 21 may be 7"×5.75". The inner boundary of the rim 21 may be 5.5"×4.25". The rim 21 is preferably semi-rigid on the lateral bands 33a,b and flexible on the end bands 33c,d. The rim 21 may be fabricated from various materials including plastic, rubber and aluminum. A rubber gasket 31 may be attached to underside of rim 21. The rubber gasket 31 may be 1/16 inch thick and provide additional padding and electrical insulation for the victim 10 as providers of medical assistance may use CCPRS concurrently with electrocardiographic monitoring (ECM) and electrical defibrillation (shocking the heart). Adhesive strips 32a,b are bonded to the underside of rim 21 along the two lateral bands 33a,b of rim 21. The chest-positioner/pad unit 20 may be formed from a single piece of plastic, and adhesive strips 32a,b attach to the underside of lateral rim 21/gasket 31 and adhesive strip 26 attaches to the underside of sternal pad 23. X-ray lucent materials should be used where possible. Markings on rim 21 will indicate proper positioning of the chest-positioner/pad unit 20 on the anterior chest wall 12. The sternal pad 23 is positioned on the lower half of the sternum 14. The rim 21 of chest-positioner/pad unit 20 attaches to the anterior chest wall 12 by adhesive strips 32a,b.

An elastic (rubber or plastic) sheet 22 stretches across top of rim 21. The chest-positioner/pad unit 20 is radiolucent and disposable. Sternal pad 23 attaches to the under side of the center of chest-positioner/pad unit 20.

Sternal pad 23 is composed of Neoprene rubber or biocompatible plastic, and will meet FDA standards. The top portion 24 of sternal pad 23 is flat and affixed to the elastic sheet 22. The base 25 of sternal pad 23 is 0.5" thick, 2.5" wide and 3.5" in length. Base 25 of sternal pad 23 has convex margins 25a and contains adhesive strip 26 which attaches to the anterior chest wall 12.

The socket 27 attaches to the top of the elastic sheet 22. Socket 27 may be fabricated from plastic, metal or hardwood material. Socket 27 is 0.5" tall, 2.5" wide and 3.5" in length. Socket 27 has walls 28 which define a cavity which may be 0.25" deep, 2" wide and 3" in length. Electrical, mechanical or manual compression devices 40 may snap into the socket 27.

Figure 5:
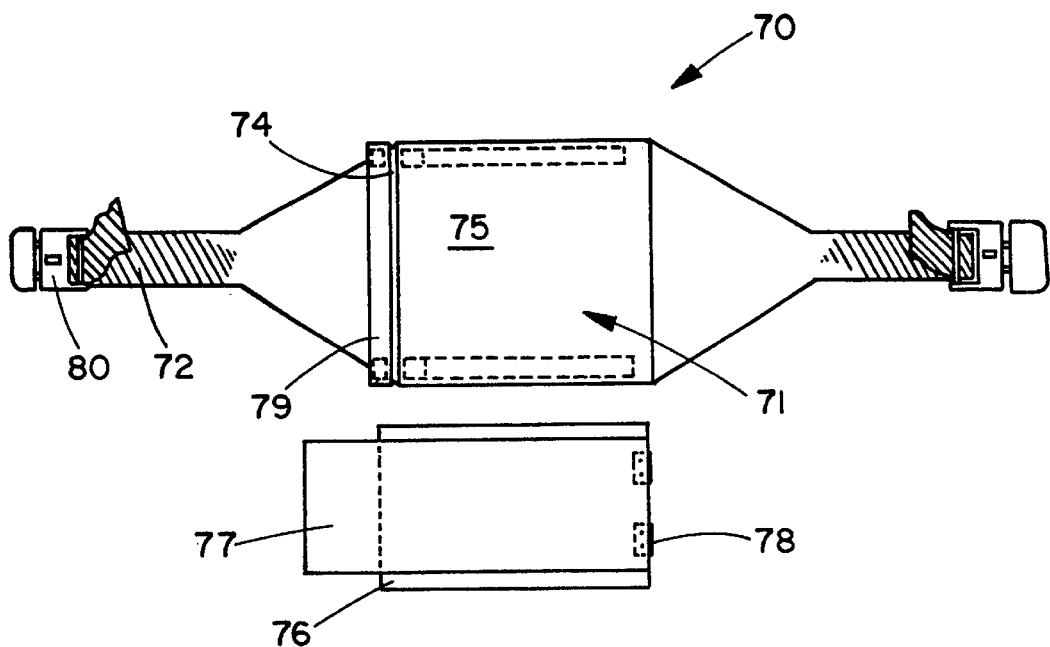
FIG. 5 is a top view of the back strap with the stiffeners removed from the pocket.

Referring to FIGS. 2 and 5 dorsal/backstrap 70 secures via connector 80 to compression device 40. Compression device 40 is snapped into socket 27 of the chest-positioner/pad unit 20 on the chest 12 of victim 10. The dorsal strap 70 is a fabric or plastic band which may be up to 42" in length. Fabric is preferred because it is durable, flexible, disposable, and economical. The middle section 71 of dorsal strap 70 may be 10" in length and 8" wide. Dorsal strap 70 tapers from a 6" wide middle section 71 to a 2" wide end section. The 2" wide strap section 72 may 10" in length, attaching to the connector 80. Middle section 71 of strap 70 includes a first 74 and second 75 piece defining a pocket (See FIG. 2).

Two stiff plastic pieces 76 and 77 are hinged together at their ends and inserted into the pocket. First plastic piece 76 is rectangular and may have dimensions of 6" wide and 10" in length. Second plastic piece 77 is rectangular and may have dimensions of 5" wide and 12" in length. Second plastic piece 77 is thinner and longer than first plastic piece 76. First plastic piece 76 rests on top of second plastic piece 77 and is positioned closest to the victim's body 10. Flap 79 folds over first and second plastic pieces 76 and 77. Plastic pieces 76 and 77 are connected by hinge 78 at the ends and provide a simple support or stiffener whereby the recoil spring 90 may be quickly inserted into the pocket of dorsal strap 70. Dorsal strap 70 connects to the compression device 40 via connector 80.

Figure 6:
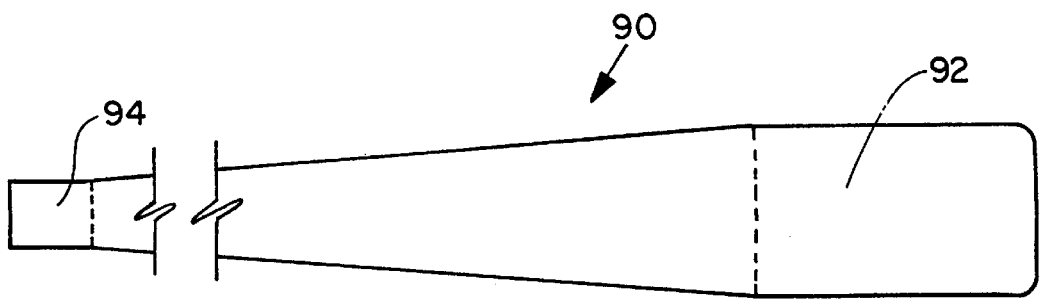
FIG. 6 is a top view of an uncoiled recoil spring.

Referring to FIG. 6, an uncoiled view of the recoil spring 90 is shown (FIGS. 1 and 2 show installed views). The recoil spring 90 is a tapered or semi-triangulated sheet of spring steel or flexible composite plastic. Base portion 92 is 6"×10". Upper end 94 is approximately 3" long and up to 2" wide. Referring to FIG. 2, upper end 94 is bent to form a hook 96. The recoil spring 90 tapers from 6" wide at the base portion 92 to ½–2 inches wide at the upper end 94. Other types of recoil devices may also be used.

As illustrated in FIG. 2, base portion 92 slips into the dorsal strap 70 pocket between the plastic pieces 76, 77. The recoil spring 90 curves around the right side of the thorax 16 upward to upper end 94. Upper end 94 hooks under bail 98 of compression device 40. The tapered design of spring 90 allows greater rigidity at lower end 92, flexibility at upper end 94 and stability for the whole system.

Recoil spring 90 lifts the compression device 40 away from the anterior chest wall 12. Lifting the compression device 40 likewise exerts an upward force on chest-positioner/pad unit 20. Chest-positioner/pad unit 20 is adhered to anterior chest wall 12 of victim 10 by adhesive strips 26, 32a,b. The result is that an upward force is exerted on the anterior chest wall 12 of the victim 10. The preferred force exerted on the anterior chest wall 12 is from two to ten pounds. If the compression device 40 weighs six lbs., then a recoil spring 90 which creates an up lift of approximately eight to sixteen lbs. may be used.

Recoil spring 90 lifts compression device 40 and anterior chest wall 12 during relaxation (diastole) phase of CPR. This "passive" decompression enhances blood return to the chest and heart and likewise enhances air/oxygen influx. The recoil spring 90 provides a passive means to expand the chest wall 12 beyond normal diastole relaxation position. Recent studies have shown that expanding the chest beyond the normal diastole relaxation position increases blood circulation, oxygenation and gas exchange. Such studies are referred to in *Active Compression-Decompression; A New Method of Cardiopulmonary Resuscitation,* Todd J. Cohen, et. al., *JAMA,* Jun. 3, 1992-Vol. 267, No. 21, pp. 2916–2923; *Effects of Active Compression-Decompression Resuscitation on Myocardial and Cerebral Blood Flow in Pigs,* Karl H. Linder, et. al., *Circulation,* (88), 1993, No. 3, pp. 1254–1263; *A Comparison of Active Compression-Decompression Cardiopulmonary Resuscitation with Standard Cardiopulmonary Resuscitation for Cardiac Arrests Occurring in the Hospital,* Todd J. Cohen, et. al., *The New England Journal of Medicine,* Dec. 23, 1993-Vol. 329, pp. 1918–1921; *Abdominal Compressions During CPR: Hemodynamic Effects of Altering Timing and Force,* J. M. Christenson, et. al., *The Journal of Emergency Medicine,* 1992, Vol. 10, pp. 257–266; and *Effects of Various Degrees of Compression and Active Decompression on Haemodynamics, End-Tidal $CO_2$, and Ventilation During Cardiopulmonary Resuscitation of Pigs,* Lars Wik, et. al., *Resuscitation,* 1996-Vol. 31, pp. 45–47, which are intended to be incorporated herein by reference.

Figure 7:
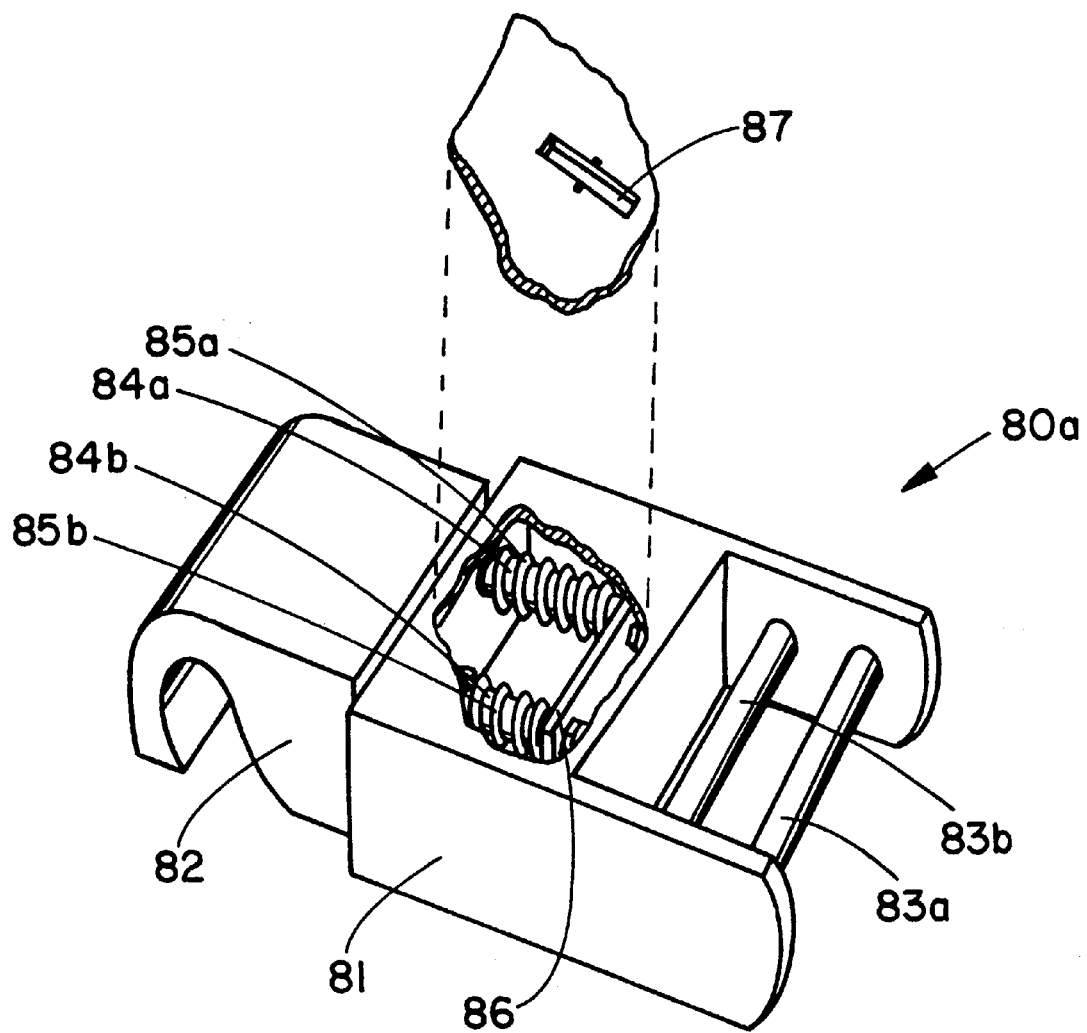
FIG. 7 is an exploded view of a tensioning buckle-hook.
Figure 8:
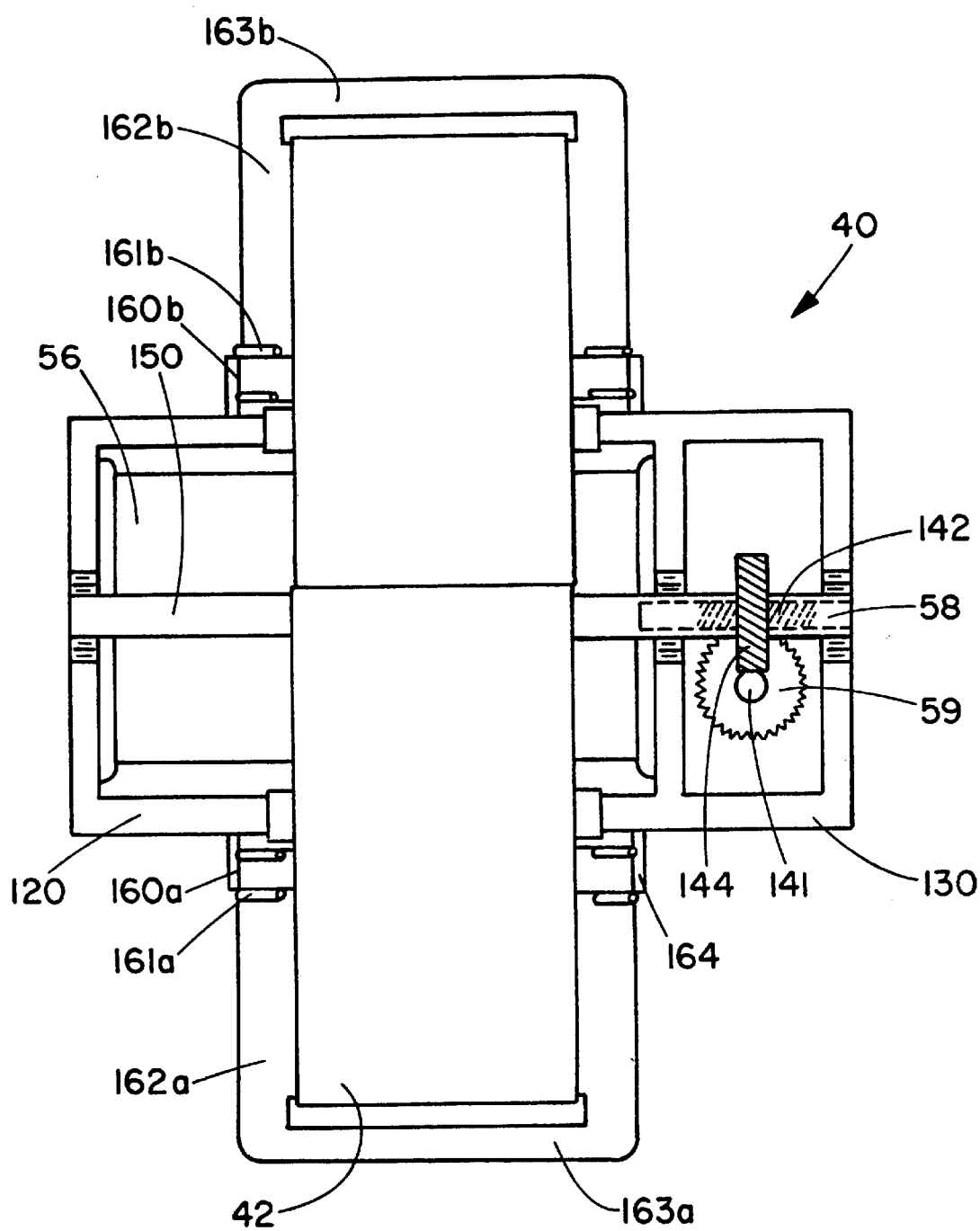
FIG. 8 is a cutaway top view of the compression device shown in FIG. 2.
Figure 9:
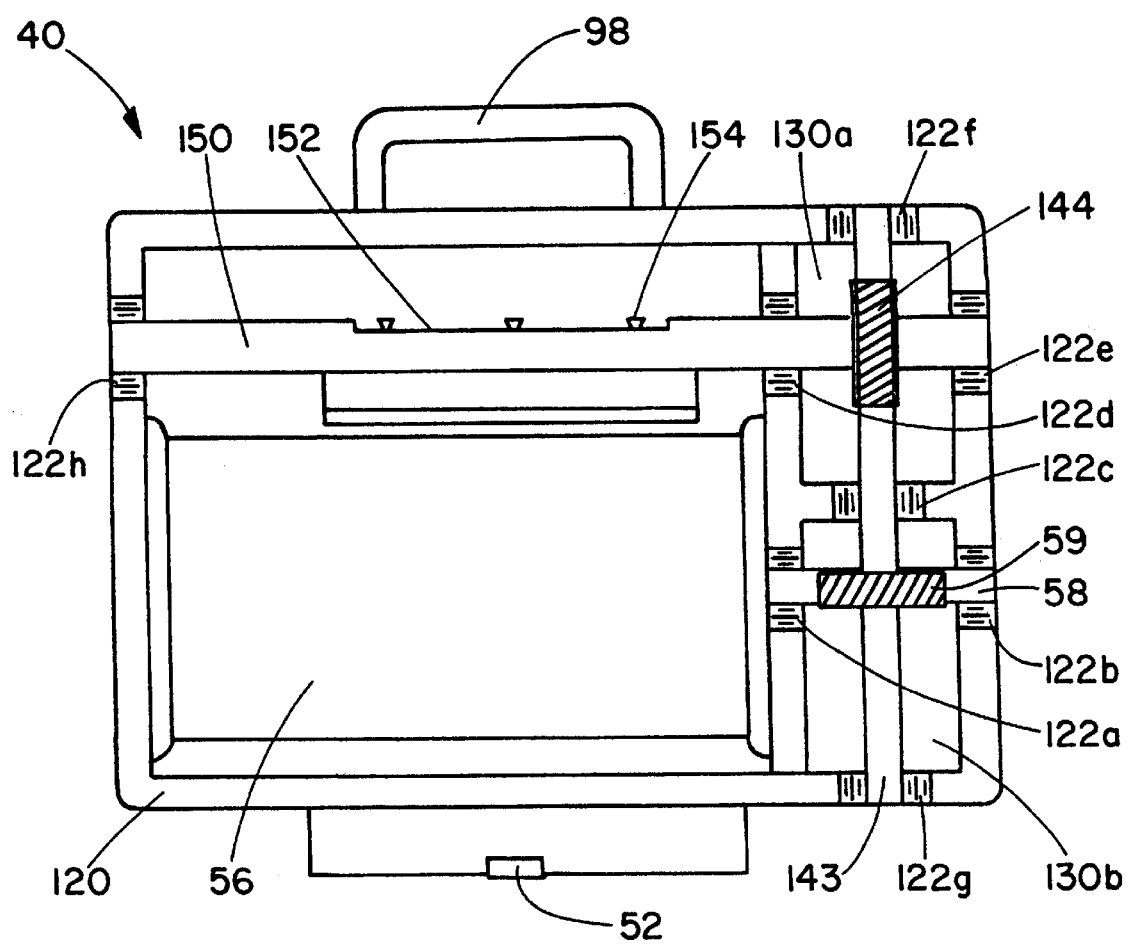
FIG. 9 is a cutaway side view of the compression device shown in FIG. 2.
Figure 10:
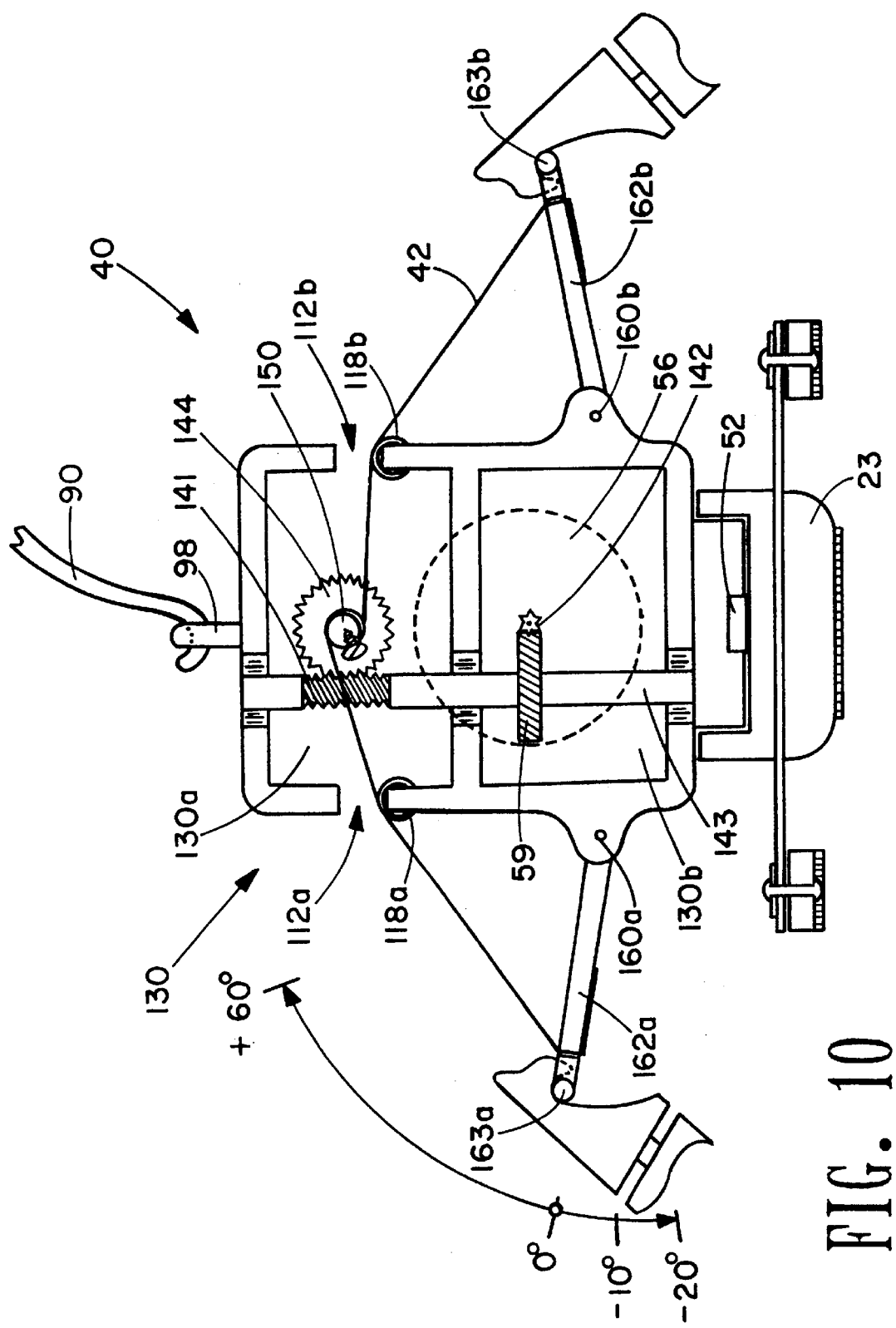
FIG. 10 is a cutaway end view of the compression device shown in FIG. 2.

Referring to FIGS. 2 and 7, one embodiment of a connector 80 is shown. This connector 80 is a quick-release tension-indicator buckle/hook 80a and includes a casing 81, hook 82, friction-grip crossbars 83a,b, two spring shafts 84a,b, two springs 85a,b, and spring plate 86. A slot 87 cut into the casing 81 allows an operator to see the spring plate 86 which becomes a tension indicator. Springs 85a,b and spring plate 86 are enclosed inside casing 81. Springs 85a,b are placed around spring shafts 84a,b. The preferred spring load is from one to two pounds. The ends of springs 85a,b contact interior wall of casing 81 and spring plate 86.

The spring plate 86 is secured to both shafts 84a,b. Spring plate 86 moves concurrently with the shafts 84a,b when tension changes. The other end of shafts 84a,b pass through holes in the end of casing 81 and attach to hook 82. As tension increases, springs 85a,b compress against the interior of the casing 81 and the spring plate 86 moves towards the hook end of casing 81. As tension decreases, springs 85a,b decompress and spring plate 86 moves toward rest position. Spring plate 86 also serves as tension indicator when viewed through slot 87. System tension must be adequate to eliminate slack in dorsal strap 70 and to secure and stabilize compression device 40. Connector 80 may be capable of supporting tensions up to one hundred pounds. Other connectors 80 having similar functional features may be implemented into the system.

Figure 11:
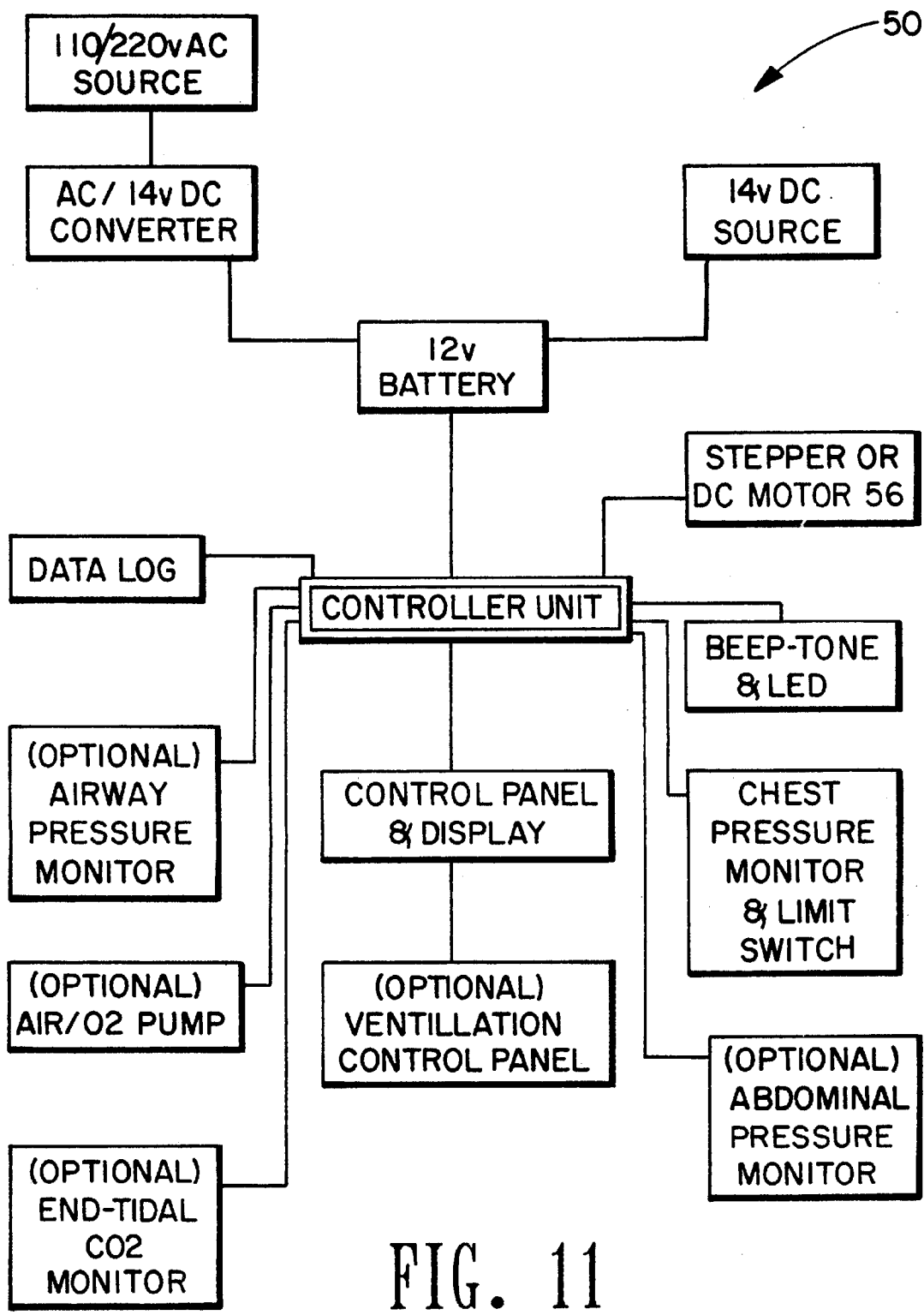
FIG. 11 is a block diagram of the electronic control system.

Referring to FIG. 11, the block diagram indicates the control system 50 which operates on a twelve Volt source. Control system 50 preferably provides audio and visual (LED) indicators and a display panel to control and monitor chest pressure, motor 56 performance, and ventilation parameters. The control system 50 may also log the time and sequence of events during its use. Either a 110/220 AC source with AC/14V DC converter or a fourteen Volt DC source may be used to power the Electrical Compression Devices 40. The design and construction of a control system 50 to be implemented into the invention is within the level of skill of one ordinary skill in the art.

Referring to FIGS. 1, 2, 8, 9 and 10, one embodiment of a compression device 40 is shown. This compression device 40 is capable of producing "hands-off" electrically driven chest compressions and generally comprises a motor box 120, gear box 130, motor 56, worm gears 141, 142, strap winding shaft 150, vertical drive shaft 143, bearings 122a–h, hinges 160a,b, torsion springs 161a,b, hinge arms 162a,b, angular sensor 164 and winding strap 42.

Compression device 40 is approximately 4" in height, 6" in length and 4" wide and is divided into motor box 120 and split gear box 130a,b sections. Motor box 120 contains motor 56, bearings 122d,h for strap winding shaft 150 and bearing 122a for motor shaft 58, and pressure sensor 52 in base of motor box 120. A stepper or servo motor may be used as motor 56.

Gear box 130 contains upper 130a and lower 130b sections. Upper section 130a of gear box 130 contains bearings 122d,e for strap winding shaft 150, strap shaft drive gear 144, a worm gear shaft 143 with worm gear 141 and bearings 122c,f. Lower section of gear box 130b contains bearings 122a,b for motor shaft 58, worm gear 142 and bearings 122c,g for shaft 143.

When motor 56 is activated and motor shaft 58 rotates, motor worm gear 142 likewise rotates. The worm gear 142 drives the lower gear 59 in lower section of gear box 130b.

A portion of the vertical drive shaft 143 in upper gear box section 130a is threaded to form a worm gear 141. As drive shaft 143 rotates, worm gear 141 drives winding shaft gear 144. The winding shaft gear 144 is fixed to the horizontal winding shaft 150. The winding shaft 150 likewise rotates when winding shaft gear 144 rotates.

Strap winding shaft 150 extends through motor box 120. Strap winding shaft 150 freely rotates between bearings 122d,e,h. A portion of the winding shaft 150 in motor box section 120 is trimmed away to form flat face 152. Strap 42 attaches to flat face 152 via anchor screws 154 which secure to flat face 152 of strap winding shaft 150. When strap 42 is wound, strap 42 passes though slots 112a,b in adjacent sides of motor box 120. Slots 112a,b are wider than the thickness of strap 42 and located near the top of motor box 120. Strap glides or rollers 118a,b are attached to motor box 120 to form the lower edge of slots 112a,b. Strap glides 118a,b decrease friction and provide smooth movement of strap 42 through slots 112a,b of motor box 120. Ends of strap 42 pass through slots 112a,b and secure themselves to the back side of the hinge arms 162a,b. Hinge arms 162a,b are attached to hinges 160a,b. Hinges 160a,b are attached to side walls of motor box 120. Hinges 160a,b provide system stability, redirect and concentrate opposing forces and help define the angles of hinge arms 162a,b with respect to the motor box 120. Sensor 164 and the hinges 160a,b can detect angular changes and report these to the control system 50. The angular displacement of hinge arms 162a,b is set by control system 50 by motor 56 rotational drive. Other devices may be implemented to limit such displacement. Tension springs 161a,b initially set hinge arms 162a,b to rest/zero position. Zero position is approximately ten degrees above horizontal. Tension springs 161a,b hold hinge arms 162a,b open during rest position. Tension springs 161a,b also provide stability during operation when hinge arms 162a,b rotate downward to rest and overshoot positions. Hinge arms 162a,b also contain hook catch rods 163a,b. Hooks 82 of quick-release tension buckles 80a attach to hook catch rods 163a,b. Dorsal strap 70 which is placed around body of the victim 10 is attached to quick-release tension buckle 80*a*. With the above configuration, the compression device 40 may be activated.

Quick-release tension buckles 80*a* attach to dorsal strap 70 and hook over hook catch rods 163*a,b* to secure the system to victim 10. Dorsal strap 70 passes around victim 10 and slack in dorsal strap 70 is removed via quick-release tension buckles 80*a*. The display 87 in quick-release tension buckles 80*a* allows the provider to achieve proper tension prior to starting motor 56.

Motor 56 weighs approximately one pound. When motor 56 is activated, motor shaft 58 rotates a predetermined amount as determined by control system 50.

Strap 42 is taken-up into the motor box as it wraps around strap winding shaft 150. The strap 42 may be replaced by chains, wire components or other materials including plastics and various reinforced strap materials. Decreased strap 42 length causes hinge arms 162*a,b* to rotate in unison upward towards bail 98 from rest position, but not more than sixty degrees from rest position. The sixty degree limitation is set by the control system 50 and the configuration of the motor box 120 and hinge arms 162*a,b*.

Consequently, an upward displacement of hinge arms 162*a,b* produces a small compressive force on the body/ribs 15 of victim 10, but a relatively large (fifty to one hundred pounds) downward force on chest wall 12 of victim 10 by sternal pad 23 for the systole phase of CPR since forces are directed by hinge arms 162*a,b* and strap glides 118*a,b* to motor housing 120.

The motor 56 reverses after hinge arms 162*a,b* reach their electronically/mechanically limited peak and/or the sternal pad 23 is driven to compress chest 12 a preferred distance ranging from 1.5" to 2" or pressure sensor 52 detects a preset pressure of up to 100 lbs. Hinge arms 162*a,b* then rotate downward away from bail 98 and overshoot past rest (zero) position. The overshoot is assisted by recoil spring 90 lifting the compression device 40 and anterior chest wall 12 (spring 90 is capable of lifting fifteen to twenty pounds). The overshoot will not be greater than negative twenty degrees past rest position. This downward overshoot of hinge arms 162*a,b* is set by control system 50 and the unwound length of strap 42. Recoil spring 90 attached to compression device 40 via bail 98 helps take up slack in strap 42 and keep it taught. The result is that chest wall 12 is passively expanded beyond normal chest relaxation position during diastole.

An optional dust boot cover (not shown) may be applied around or over hinges 160*a,b* and hinge arms 162*a,b*. A suitable dust boot cover is flexible (made of rubber or the like) and prevents dust or other particles and foreign bodies from interfering with hinge function.

Figure 12:
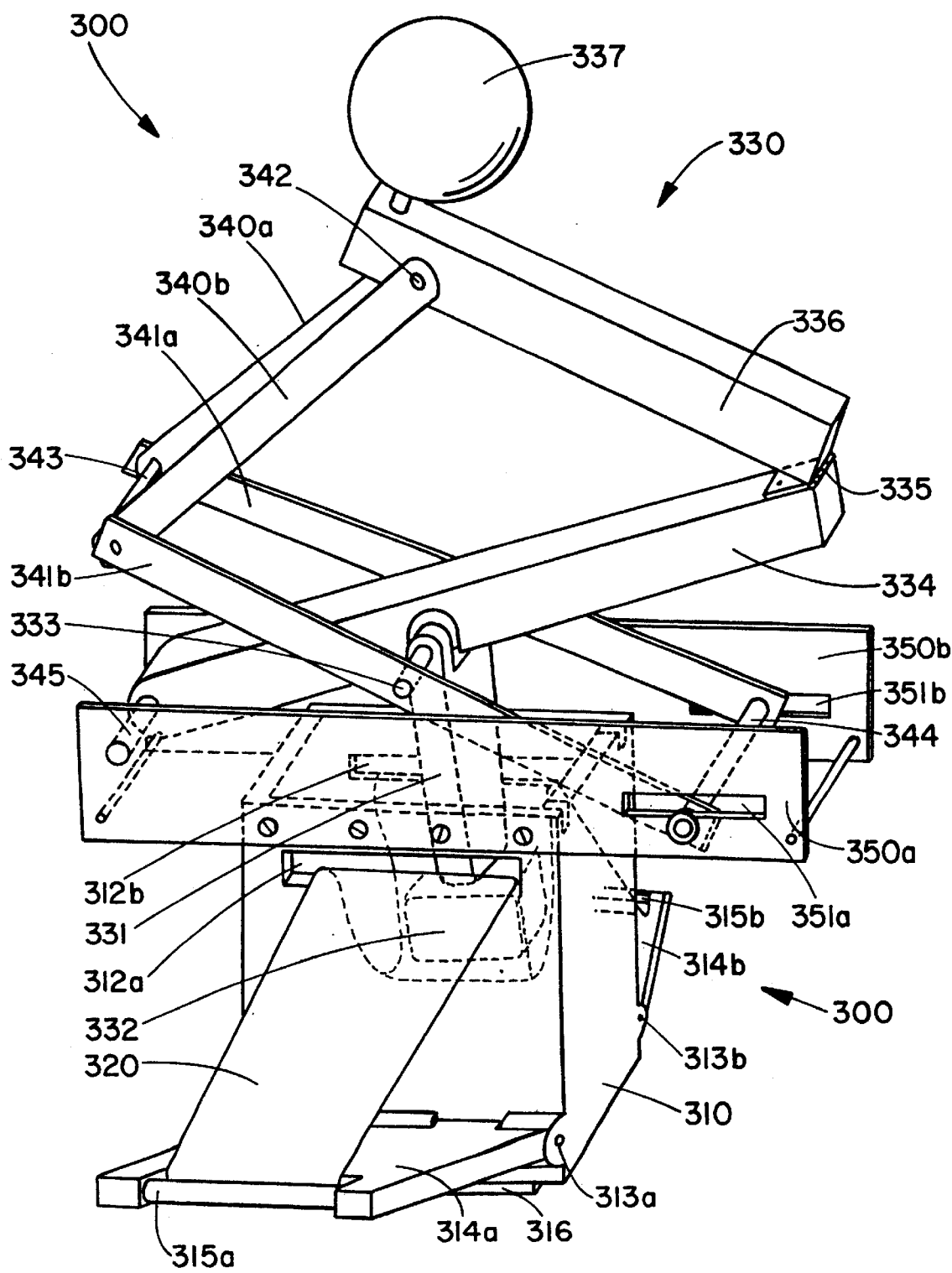
FIG. 12 is a perspective view of a mechanical compression device with a compression augmentation lever apparatus.

Referring to the FIG. 12, mechanically driven chest compressions may be administered in one embodiment by inserting compression augmentation device (CAD) 300 into socket 27 of chest-positioner/pad unit 20. CAD 300 may replace or provide backup to compression device 40. CAD 300 generally comprises a box 310, strap 320, pump handle system 330 and plunger 331. Box 310 is approximately three inches wide, four inches in length and four inches in height. Strap 320 is two inches wide, and passes through horizontal slots 312*a,b* (with or without rollers) in box 310. Slots 312*a,b* are on two parallel faces of box 310 approximately one-half inch from the top of box 310. Hinges 313*a,b* and hinge arms 314*a,b* attach to respective sides of box 310 similarly to configuration of the motor box/hinges on the compression device 40. Cross bars 315*a,b* are attached to hooks 82 of connector 80 on dorsal strap 70 to secure CAD 300 to victim 10. The foot plate 316 of box 310 sits in socket 27.

In operation, CAD 300 is snapped into socket 27. Connector hooks 82*a,b* are attached to crossbars 315*a,b* and cinched down to a predetermined resting tension as indicated by slot 87. In this resting position, the strap 320 passes straight through slots 312*a,b* so that footpad 332 rests on the middle of strap 320. Footpad 332 may be anchored to strap 320 by glue or screw(s) (not shown). The plunger arm 331 is attached via a hinge pin 333 to the middle part of lower lever arm 334. Lower lever arm 334 is attached by hinge 335 to upper lever arm 336. Hand grip 337 is attached to the upper end of upper lever arm 336. Also attached to the upper end of upper lever arm 336 by hinge pin 342 are stabilizer arms 340*a,b*. Hinge pin 343 attaches upper stabilizer arms 340*a,b* to lower stabilizer arms 341*a,b*. Lower stabilizer arms 341*a,b* pass downward toward guide rails 350*a,b*. Hinge pin 333 is attached, at midpoint of the lower stabilizer arms 341*a,b* and at the lower end is pin 344 which slides in slots 351*a,b*. The guide rails 350*a,b*, are firmly affixed to the upper rim of box 310. The lower end of lever arm 334 is attached to guide rails 350*a,b* by hinge pin 345.

At the rest (diastole) position the pump handle system 330 is fully extended upward a distance predetermined by the position of pin 344 in slots 351*a,b*. During the power stroke (systole) the handgrip 337 is pushed downward toward the victim's sternum 14 until it is stopped by the pin 344 being moved to the opposite ends of slots 351*a,b*. Plunger 331 is forced downward into the box 310 cavity, thereby drawing strap 320 into the box 310 through slots 312*a,b*. This motion raises hinge arms 314*a,b* thereby lifting connectors 80. This tightens dorsal strap 70 and forces the foot plate 316 downward toward the sternum 14, increasing the downward force of sternal pad 23. The mechanical advantage of handgrip 337 motion to plunger 331 motion is approximately three to one. This serves to amplify the operator's applied force, so that a sternal force of approximately sixty pounds requires only about twenty pounds of force on the handgrip 337.

An alternate manual backup system for CCPRS is realized by snapping a simple palm pad (not shown) into socket 27. Palm pad may be of various materials including wood, plastic, ceramic, etc. Palm pad may be round or dome-shaped to comfortably fit the contour(s) of the hand.

Figure 13:
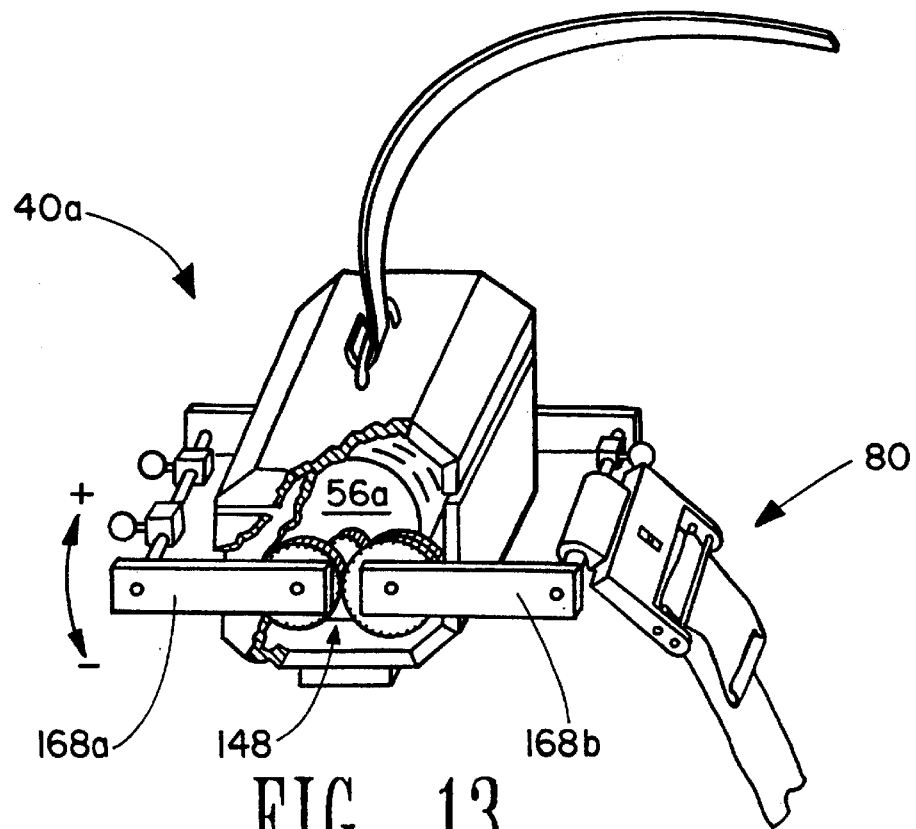
FIG. 13 is a perspective view of another embodiment of a compression device.
Figure 14:
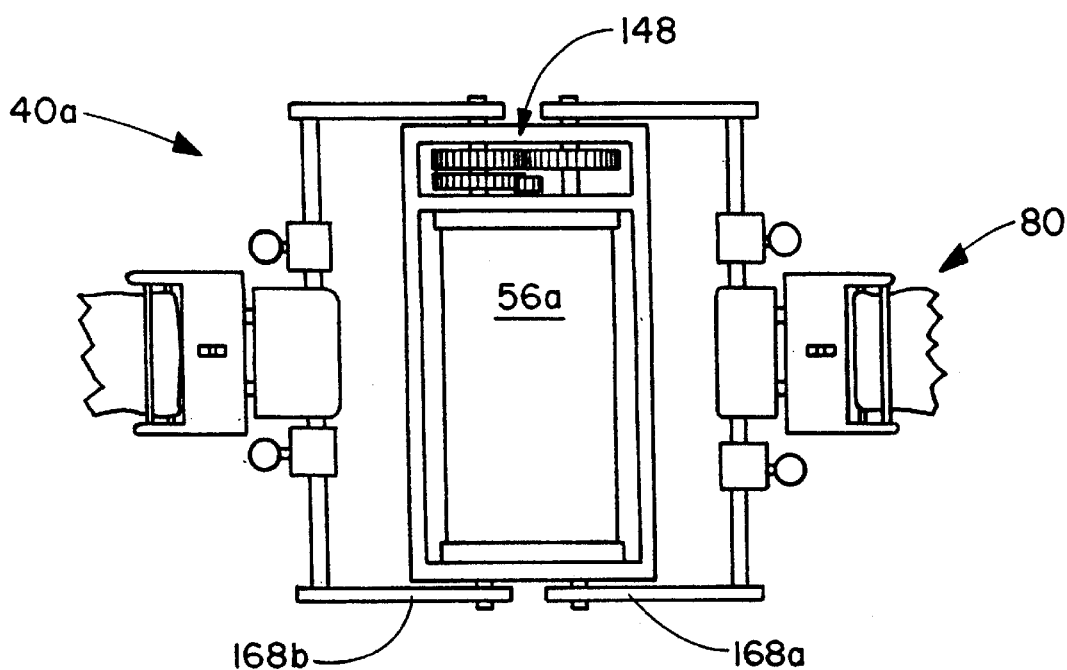
FIG. 14 is a top, sectional view of the compression device shown in FIG. 13.

Referring to FIGS. 13 and 14, an alternative compression device 40*a* generally includes a motor 56*a*, gear system 148 and rocker arms 168*a* and *b*. In operation, motor 56*a* drives gear system 148 which drives rocker arms 168*a,b*. In many other ways, compression device 40*a* is similar to compression device 40.

Chest-positioner/pad unit 20 provides proper positioning over sternum 14 and distributes forces over anterior chest wall 12 to protect ribs 15 and costal cartilage 16 from fracture during CPR.

Referring to FIG. 1, an adjustable abdomen compression/binder device 500 may be applied to victim 10 after CPR has been initiated and after endo-tracheal intubation has been performed. Abdomen compression 500 is an extended Disposa-Cuff 2505 made by CRITIKON. Other abdominal binder or compression devices may also be utilized. The effect of applying abdominal compression device 500 is an increase in abdominal pressure forcing blood from abdomen into chest during diastole. Increased blood return to the chest increases cardiac output and improves CPR. Abdomen compression device 500 comprises a wrap containing a blood pressure cuff (cuff/wrap 502), pressure gauge 510, bulb pump 520 and Velcro type attachments (not shown). Velcro attachments are on ends of cuff/wrap 502. Cuff/wrap 502 is of sufficient length to wrap around victim 10 of various sizes. The length of cuff/wrap 502 may be adjusted to accommodate a waist of up to fifty inches girth. Cuff/wrap 502 is wrapped around victim 10 snugly and secured with Velcro attachments. Bulb pump 520 is repetitively squeezed until a desired pressure is attained. Pressures of approximately 50–100 Torr may be provided.

Referring to FIGS. 1 and 11, an optional respirator system (not shown) such as those known to one of ordinary skill in the art of rescue and resuscitation may be used with the CCPRS. A bag-valve-respirator (not shown) or other available respirator may be employed to provide breathing in concert with chest compressions.

The above disclosed invention enables providers to administer effective CPR with less effort. Besides overcoming weaknesses in the prior art, other novel and unique capabilities are realized with the CCPRS.

First the CCPRS may be used in hospitals, homes or mobile units where space is often limited. Providers are able to administer CPR with the CCPRS in an airplane, ambulance or other mobile unit. Typically space is very limited in mobile units considering space occupied by providers, seats and equipment. Many of the prior devices lack mobility. They further lack adaptability for positioning the patient in limited space. With the small size and adaptability of the CCPRS, victims may be positioned supine, upright or at various angles to accommodate mobility and space limitations. A stable platform or firm back board is not required for the electrical compression device 40.

Second, a significant benefit of positioning the victim at varionus angles is that the head of the victim is not required to be at the same horizontal level as the heart. The head may now be elevated above the heart, thereby enhancing blood return from the head. Since CPR elevates intra cranial pressure, as reported in the publications identified above which are intended to be incorporated herein by reference, elevation of the head may help reduce this undesired effect.

Third, the CCPRS could also be used to transport donor organs. Typically donor organs are removed from the donor body after death and placed in a cooler, then transported. With the CCPRS, the whole body could be transported while the organs continue to be perfused as occurs in vivo. When the body reaches its destination, the CCPRS is disengaged and organ(s) are removed from the body for transplantation. This allows for preservation of organs in a more natural state until just prior to transplant.

Fourth, the CCPRS may provide short-term left ventricular assistance during electro mechanical dissociation. The EKG can be employed to trigger chest compressions. Thus, the CCPRS may be employed to augment contractions of a failing heart.

Fifth, the gentle application of CPR via CCPRS may allow thrombolytic drugs to be given during CPR.

Figure 15:
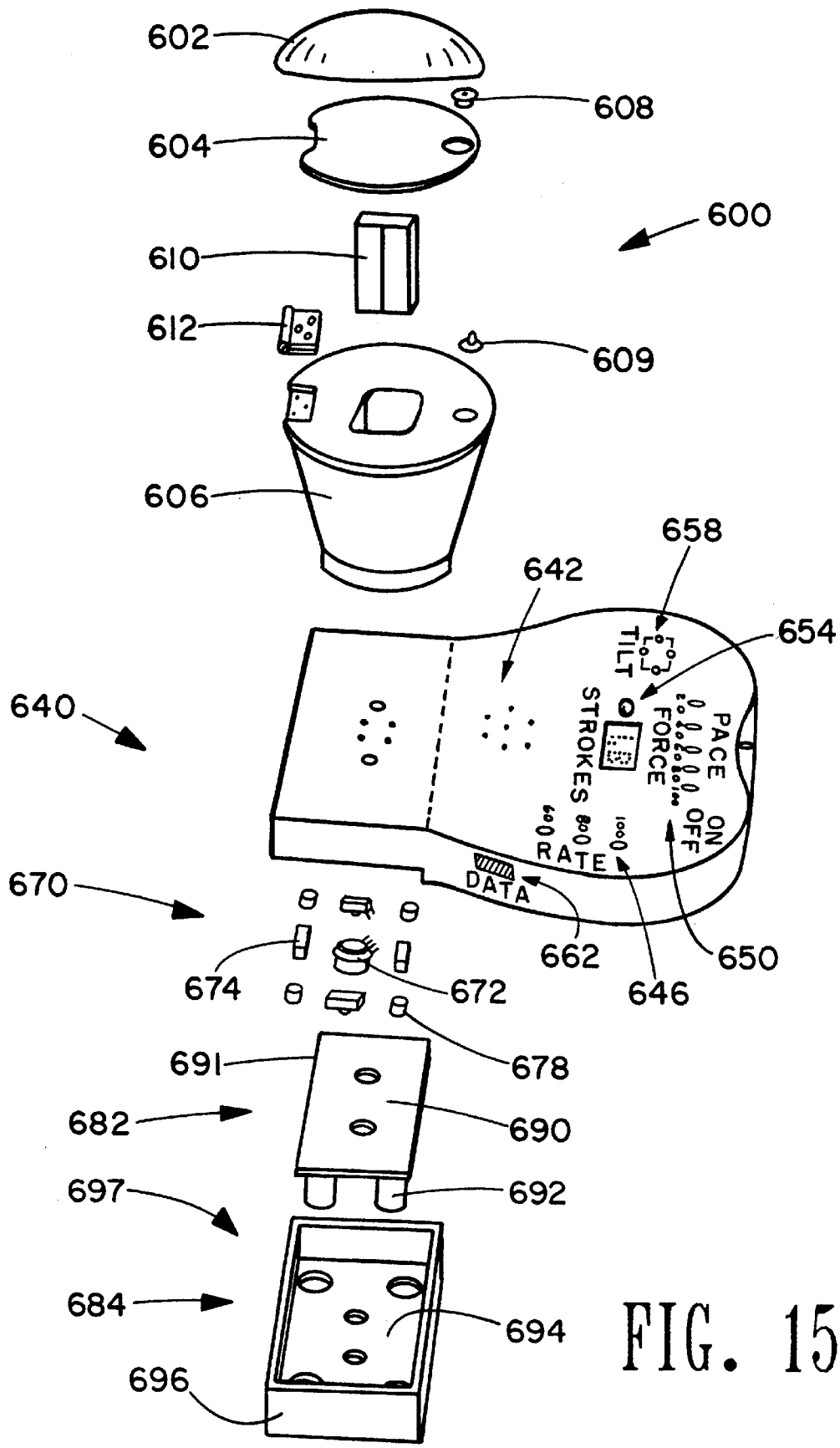
FIG. 15 is an exploded view of another embodiment of the invention.
Figure 16:
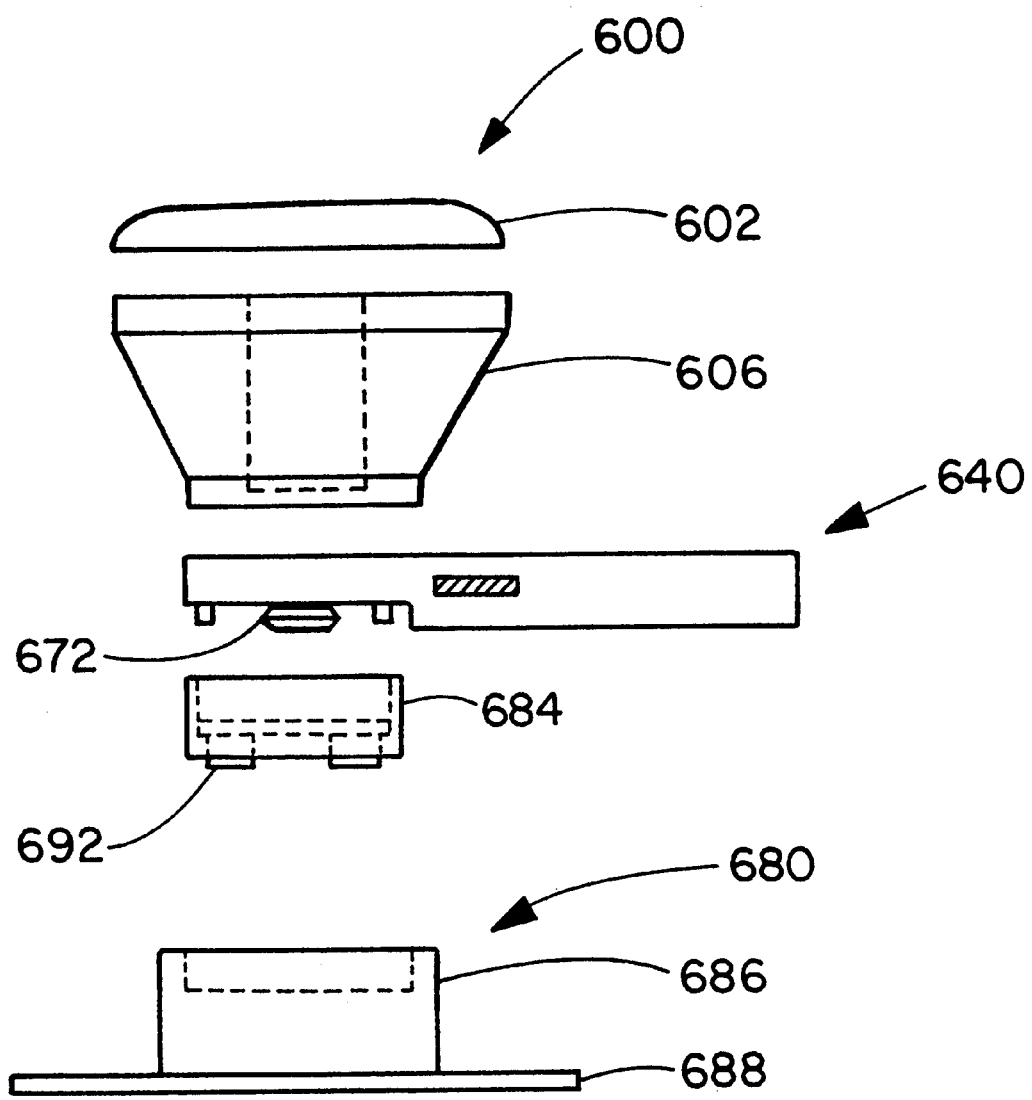
FIG. 16 is an exploded elevational of view of the embodiment shown in FIG. 15.

Certain changes can be made to the invention to address issues such as proper chest positioning; applying proper force at the proper time in a proper downward direction; and in maintaining such proper forces at the proper time in the proper direction. Referring to FIGS. 15 and 16 another embodiment of the invention is shown. This embodiment generally includes a grip 600, an electronic display module 640 and a position assurance device 680.

Figure 17:
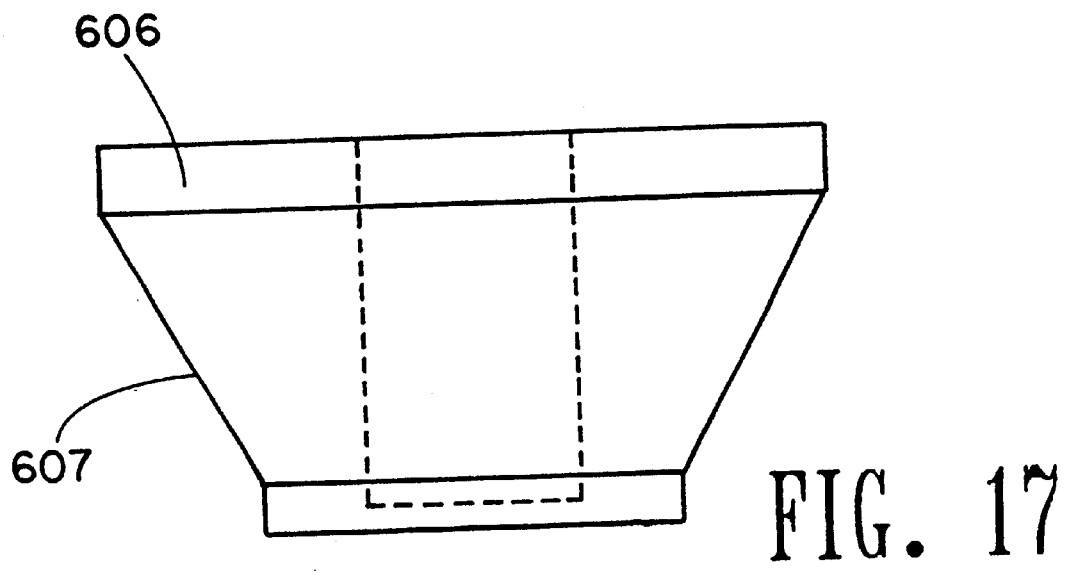
FIG. 17 is an elevational view of the grip base.
Figure 18:
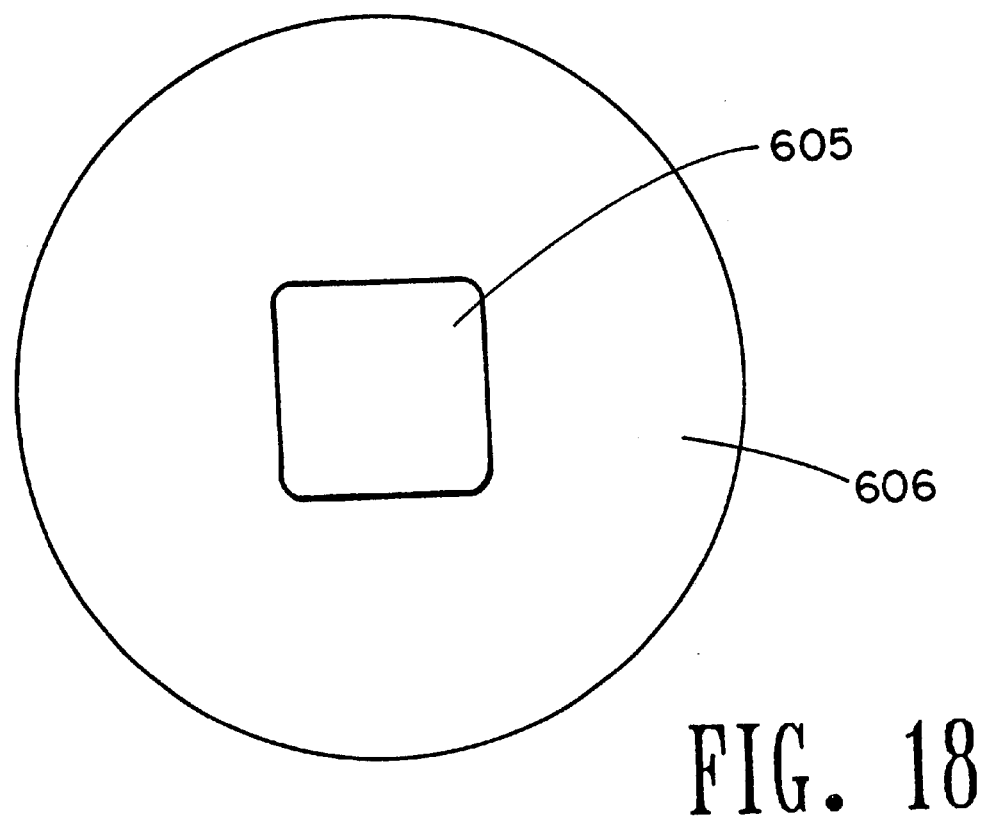
FIG. 18 is a top view of the grip base.
Figure 19:
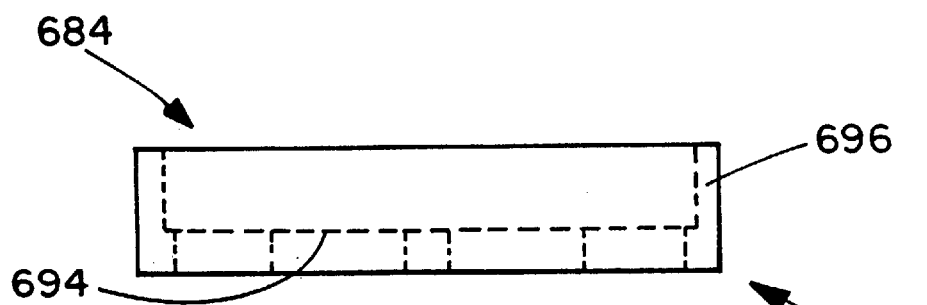
FIG. 19 is an elevational view of the sensor cover.

The grip 600 is made to fit the palm of the hand and includes a palm grip or grip cover 602, a gasket 604 and a grip base 606. The grip 600 also includes snaps 608 and 609, battery pack 610 and a hinge 612. The palm grip 602 is a rounded disk for fitting the palm of the hand and may be made of pour molded polyurethane. The grip base 606 may be made of A.B.S. and cut from a lathe. Generally, it may have a top diameter of 3½ inches, a bottom diameter of 2 inches and a height of 2⅛ inches. The sidewall 607 may be angled at 27 degrees from the vertical (see FIGS. 17 and 18). The grip base 606 includes a battery compartment 605.

The electronic display module 640 allows one to determine and measure the force applied during a chest compression, to display the force so that one can determine whether they are applying a proper barehand force, feed back on whether the force is being applied at the proper rate and a way to measure and display whether the force is applied in the proper direction, all under emergency conditions. The circuit design for same is within the range of one of ordinary skill in the art.

The display module 640 generally includes a display face 642, an array of sensors 670, a foot piece 682, and a sensor cover 684.

Electronic display module 640:
(a) functions as a metronome to report the pace selected by a user (such as, for example, 60, 80, or 100 communications per minute). The report may be by light 646 and/or sound.
(b) displays stroke or compression force with running light display 650. This gives the user feedback as to whether they are applying an appropriate barehand force.
(C) counts strokes up to, for example, 15 strokes and reports at counter display 654, then gives a report, for example, by a double beep to remind single rescuer to give two breaths; (it may reset to zero if for example there is no stroke for three seconds). One may turn the counter off for two rescuers.
(d) monitors force and angle of applied force, and alarms if force from grip is applied with a "TILT" condition and reports direction of tilting with LED array 658 (four directional display shown).
(e) has data output 662 to allow interface with PC computer or laptop. This is useful when it is desired to be in a teaching mode.
(F) may be set to turn itself off if no strokes are detected, for example, in five minutes.

The array of sensors 670 includes a pressure sensor 672 to determine/measure the pressure to be transduced to a force signal. The pressure sensor 672 is preferably a Motorola MX200 and can be set to start reading or displaying at various levels, such as for example, twenty pounds at running light display 650. The array 670 also includes multiple micro switches 674 (in this case four are shown). The amount and direction of force applied is used to determine the triggering of each micro switch 674. In this case, the four micro switches 674 transduce a signal to the four LED's 658 mounted on the display face 642 to indicate whether and in which direction the tilt limits have been violated. The array of sensors 670 may be buffered by bumpers 678. The bumpers 678 may be made of cylindrical neoprene rubber to provide support and stability to the array 670. The display face may be made of A.B.S. or other suitable materials. The array of sensors 670 may be adhered to the underside of the electronic display module 640.

The foot piece 682 has a foot plate 690 which contacts pressure sensor 672 and four, for example, Neoprene bumpers 678. Each of the four top edges 691 of the foot plate 690 should not contact one of the four micro switches 674 unless excessive downward force is applied to the grip 600 or device such as in a "tilt" condition. This configuration enables each micro switch 674 to determine a "tilt" condition in its corresponding direction. Whether or not a "tilt" condition exists is a variable dependent on the applied force vector which includes the quantum of force and the angle of force. One of ordinary skill can determine the appropriate conditions.

The sensor cover 684 has a base 694 and four sidewalls 696. Four holes (e.g. 9/16" diameter) are made through the base 694 proximate each of the corners 697. The legs 692 in the foot piece 682 correspond with and when assembled protrude through the holes in the sensor cover 684 leaving a 1/32 inch gap between each hole and each leg 692 allowing a pressure relief while maintaining alignment of the foot piece 682. The legs 692 then rest on the base 685 of the chestpiece socket 686. This allows the foot piece 682 to wobble during CPR operations so that edges 691 move for potential interaction with microswitches 674 for determining whether the force is applied in a correct direction or whether a "tilt" condition exists. The foot piece 682 and sensor cover 684 may be made of A.B.S. or metal or some other suitable material.

The position assurance device 680 generally includes a chestpiece socket 686 and a chestplate 688.

The chestplate 688 may be made of PVC, polyethylene or a similar semirigid but flexible plastic and may be 5 inches by 6 inches by 1/8 inch thick. The chestplate 688 may be releasably adhered to the chest of the patient, protects the thorax including the ribs of the patient, does not interfere with defibrillator pads, and is transparent to x-rays.

Figure 20:
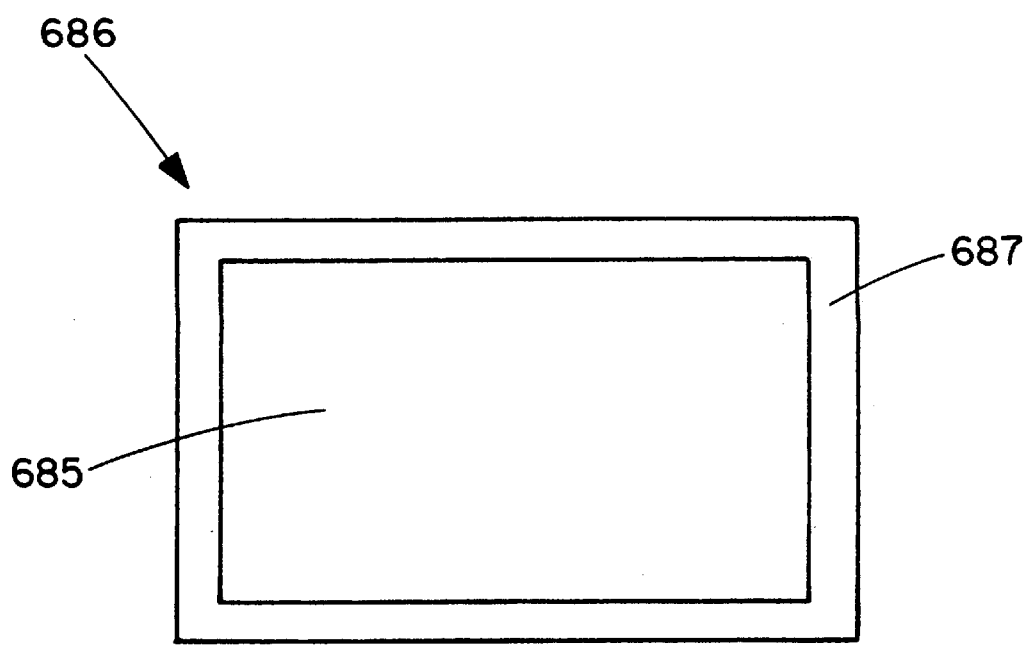
FIG. 20 is a top view of the chestpiece socket.

The chestpiece socket 686 may be made of a rigid plastic such as PVC or A.B.S. and attaches to the chestplate 688. Socket 686 (FIG. 20) has a base 685 and four sidewalls 687 defining inner dimensions of 3 1/16" by 2 1/16" by 3/8" deep to receive sensor cover 684 with a loose fit. Sensor cover 684 fits within socket 686 and legs 692 rest on the base 685 of the socket 686.

In conclusion, therefore, it is seen that the present invention and the embodiments disclosed herein and those covered by the claims are well adapted to carry out the objectives and obtain the ends set forth. Certain additional changes can be made in the subject matter without departing from the spirit and the scope of this invention. It is realized that changes are possible within the scope of this invention and it is further intended that each element or step recited in any claims is to be understood as referring to all equivalent elements or steps. The claims are intended to cover the invention as broadly as legally possible in whatever form it may be utilized.

What is claimed is:

1. An apparatus for assisting with the administration of CPR to a patient comprising:
    (a) a chest positioner unit conformable to the shape of a patient's chest to position the apparatus on the sternum comprising a sternal pad that rests on the sternum of the patient, a socket for connecting with the chest compression device, and an elastic sheet having dimensions larger than the sternal pad or the socket and mounted between the sternal pad and the socket;
    (b) one or more straps for securing a chest compression device to the patient's chest;
    (c) said chest compression device connected with the chest positioner unit, said device having arms connected with the device and extending laterally from each side of the device, each said arm having a first end pivotally connected with the device and a second end connected with one of said strap or straps; and
    (d) a control assembly operably connected with the chest compression device to actuate the chest compression device to deliver chest compressions at a preferred stroke rate.

2. The apparatus of claim 1 wherein the chest positioner unit is radiolucent.

3. The apparatus of claim 1 wherein the chest positioner unit is electrically insulating.

4. The apparatus of claim 1 wherein the chest compression device is electrically actuated by the control assembly.

5. The apparatus of claim 1 wherein electrical actuation of the chest compression device moves the arms of the device from a rest position to an active position causing the strap wrapped around the chest of the patient to tighten and the chest compression device to apply a downward force to deliver an effective chest compression.

6. The apparatus of claim 1 wherein the chest compression device contains a pressure sensor.

7. The apparatus of claim 1 wherein the control assembly further actuates the chest compression device to deliver chest compressions at a preferred force.

8. The apparatus of claim 1 wherein the strap contains a rigid central section located at the back of the patient when the apparatus is employed.

9. The apparatus of claim 1 wherein the strap is connected with the chest compression device using tension-indicating hooks.

10. The apparatus of claim 1 further comprising a recoil spring for decompressing the chest beyond normal diastole position.

11. The apparatus of claim 1 wherein the recoil spring has a first end and a second end where the first end is connected with the rigid central section of the strap and the second end is connected with the chest compression device.

\* \* \* \* \*